United States Patent [19]

Tritsch

[11] 4,010,753
[45] Mar. 8, 1977

[54] DISPOSABLE DIAPER HAVING ADHESIVE TAB FASTENERS WITH BUILT-IN RELEASE SYSTEM

[75] Inventor: Ludwig Tritsch, Wilmette, Ill.

[73] Assignee: Johnson & Johnson, New Brunswick, N.J.

[22] Filed: Feb. 19, 1976

[21] Appl. No.: 659,314

[52] U.S. Cl. .............................. 128/284; 128/287; 24/DIG. 11

[51] Int. Cl.² .......................................... A16F 13/16

[58] Field of Search ......... 128/287, 284, 290, 156; 24/DIG. 11, 67 AR, 73 VA; 117/122 P

[56] References Cited

UNITED STATES PATENTS

| 2,399,545 | 4/1946 | Davis | 128/156 |
| 3,630,201 | 12/1971 | Endres | 128/287 |
| 3,811,438 | 5/1975 | Economou | 128/156 |
| 3,943,609 | 3/1976 | Egan, Jr. | 214/DIG. 11 X |
| 3,967,624 | 7/1976 | Milnamow | 128/284 X |

Primary Examiner—Stephen C. Pellegrino

[57] ABSTRACT

A disposable diaper is provided with adhesive tab fasteners having an adhesive coating on substantially all of one face thereof. The tabs have side edges, a fixed end secured to the diaper, and a free working end which includes a distal end portion and an adjacent central portion. A plurality of elongated spacer means are adhered to the adhesive-coated surface and define exposed adhesive regions therebetween. The distal end portion is folded over onto the central portion, with the spacer means being positioned so that the spacer means on the distal end portion bridge the spacer means on the central portion and vice versa, and are in limited adhesive contact with a juxtaposed region of the adhesive coated surface at a plurality of attachment points between the points of bridging by juxtaposed spacer means.

15 Claims, 8 Drawing Figures

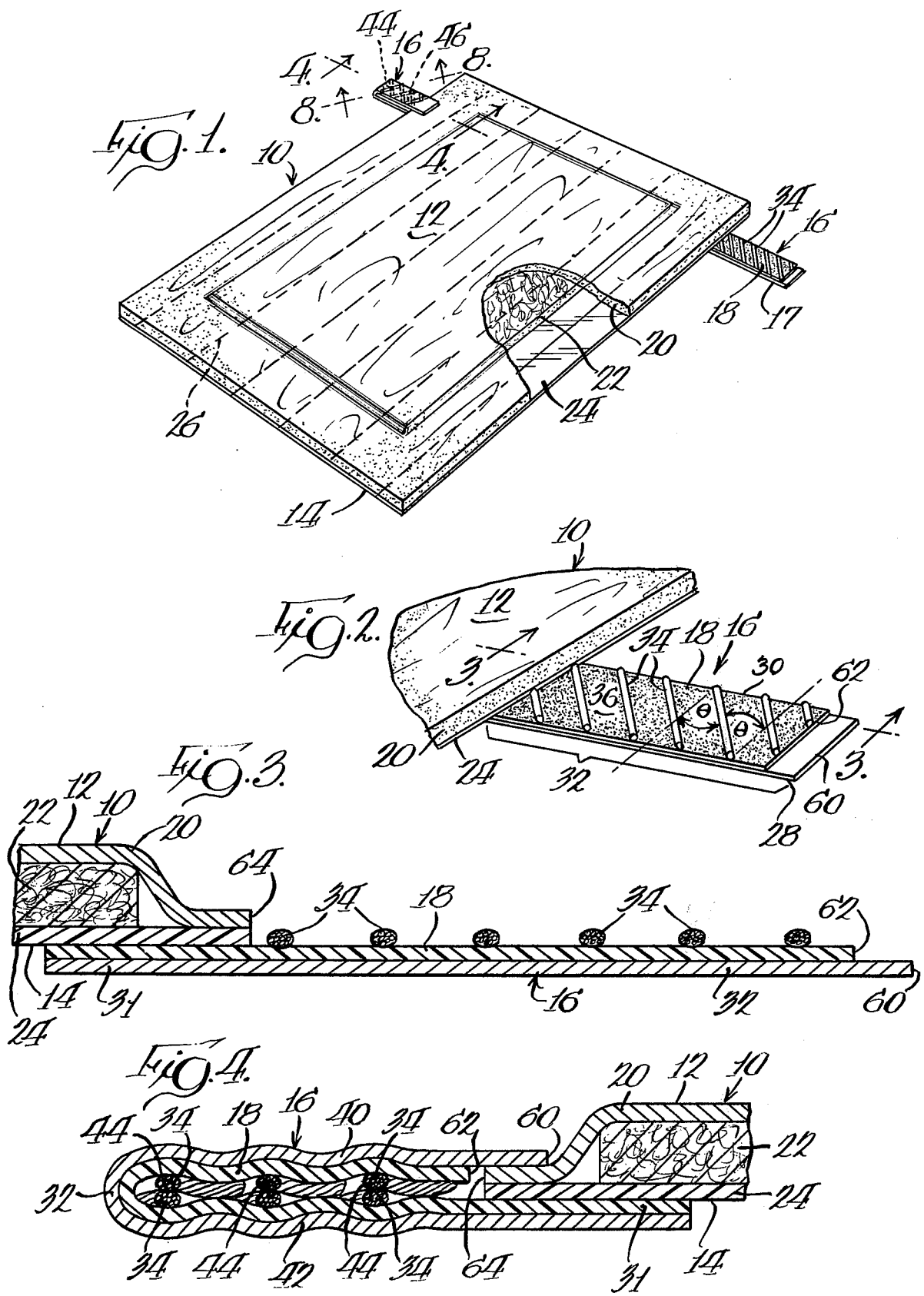

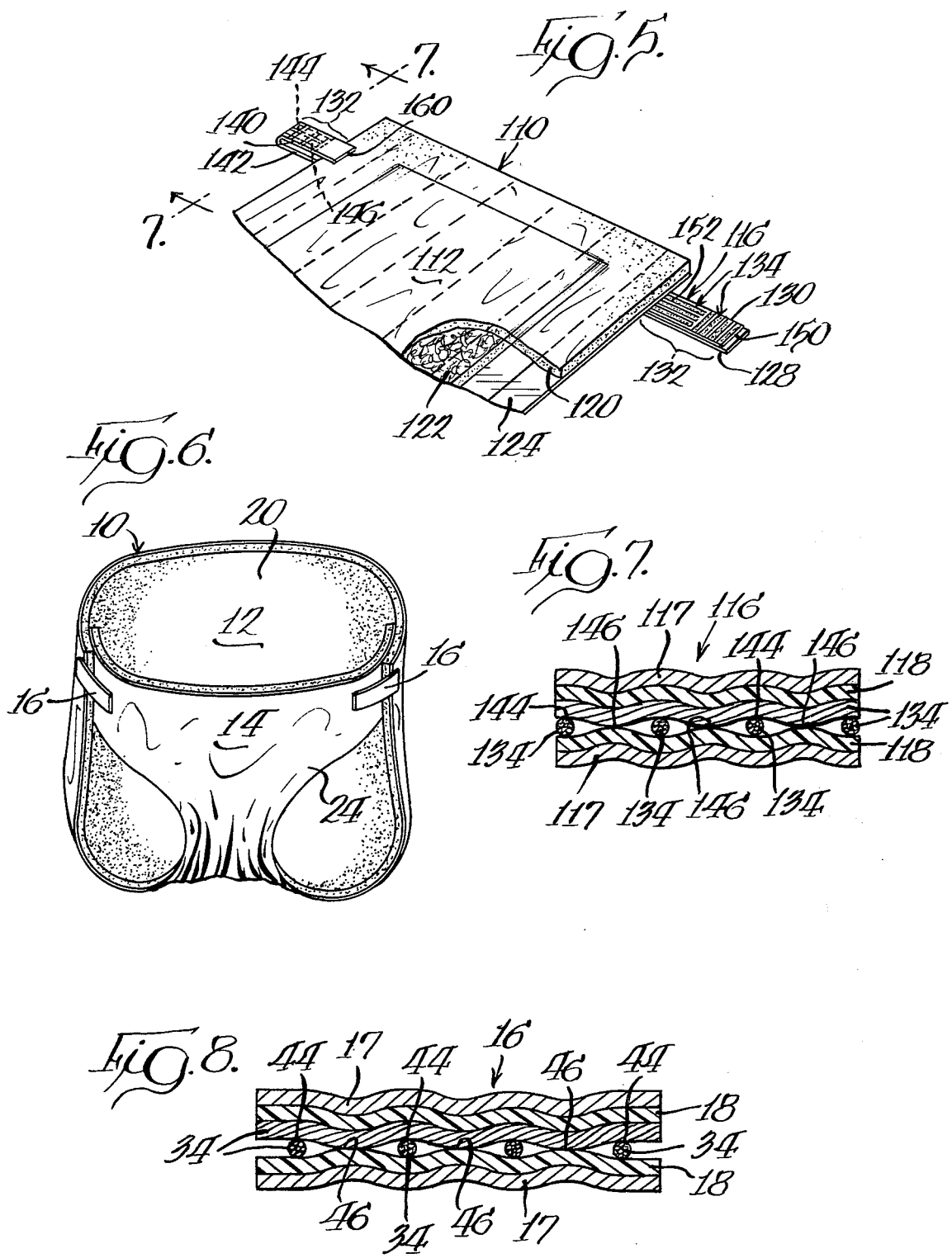

DISPOSABLE DIAPER HAVING ADHESIVE TAB FASTENERS WITH BUILT-IN RELEASE SYSTEM

BACKGROUND OF THE INVENTION

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a facing material to be brought into contact with the infant's skin, an absorptive layer of high liquid-holding capacity, and a moisture-impervious backing layer, generally made of a plastic film such as a polyethylene film. Typical disposable diaper structures are shown in U.S. Pat. No. 3,612,055 to Mesek et al. and in U.S. Pat. No. Re. 26,151 to Duncan et al.

As may be seen from the above-cited patents, it has been desired to obviate the problems that are inherent in closure systems utilizing extraneous fasteners such as safety pins, snaps and zippers. To this end, adhesive closure systems have presented acceptable solutions.

One of the most convenient adhesive systems that has been developed to date is the system, shown in the above-cited patents, in which adhesive tabs are adhered to the backing sheet extending outwardly from opposite sides of the diaper at one end thereof, with the exposed areas of the adhesive strips having cover strips thereon that are readily separable from the adhesive tabs. Disposable diapers using an adhesive closure system of this general type have the disadvantage of requiring the consumer to dispose of the cover strips when they are separated from the adhesive strips. This is an inconvenience to the consumer who is placing the diaper on an infant.

An illustrative prior art adhesive system having cover strips permanently attached to the diaper is disclosed in U.S. Pat. No. 3,646,937 to Gellert. The Gellert arrangement has the disadvantage of having the release film on the inside of the diaper, where it can possibly come in contact with an infant's tender skin. Additional disadvantages are the complexities and expense which are added to the manufacturing process by requiring each adhesive closure to be manipulated on the front side, around the edge, and on to the back side of the diaper, instead of handling it on one side only. The closure system illustrated in the Gellert patent also makes it somewhat difficult to secure the diaper around an infant, in that it requires the use of two hands to peel back the releasable end of the adhesive tape.

U.S. Pat. No. 3,853,129 to Kozak attempts to solve the foregoing problems by providing adhesive tabs having a fixed end segment attached to the diaper, a middle segment having one face covered with a mesh-like plastic material defining a system of hill portions and valley portions, and a releasable working end coated with a pressure-sensitive adhesive and releasably adhered to the hill portions in the middle segment. However, with such an arrangement the available effective adhesive area is limited, the working end of the tab may be subject to displacement transverse to the longitudinal axis, and the tab could be subjected to greater stresses when in use than when the fixed end and the working end of the tab are contiguous.

SUMMARY OF THE INVENTION

In this invention, an adhesive tab fastener for a disposable diaper is made of a single tape segment having a pressure-sensitive adhesive coating on substantially all of one face thereof. The tab fastener has side edges, a fixed end secured to the diaper, and a free working end which includes a distal end portion and a central portion. A plurality of elongated spacer means is positioned on the adhesive coated surface and is adhered thereto, and defines a plurality of exposed adhesive regions between the elongated spacer means.

The spacer means are positioned so that when the free end of the tab is folded over upon itself juxtaposed spacer means bridge one another and are in limited adhesive contact with adjacent regions of the adhesive coated surface at a plurality of attachment points. As a result, the distal end portion is secured to the central portion, yet is readily releasable from the central portion, and the entire free working end of the tab is available for adhesive securement.

In one embodiment, the spacer means are substantially parallel to one another. The spacer means preferably are uniformly spaced and disposed at an angle of about 30° to about 60° relative to the side margins of the diaper. In an alternate embodiment, a first set of parallel spacer means is disposed on the distal end portion, and a second set of parallel spacer means is disposed on the central portion, with an angle between the first and second sets of spacer means being about 90°, and one of said sets having spacer means positioned substantially parallel to the side margins of the diaper and the other of said sets having spacer means positioned substantially normal to the side margins of the diaper.

BRIEF DESCRIPTION OF THE DRAWINGS

FIG. 1 is a perspective view of an open unfolded disposable diaper in accordance with one embodiment of the invention, parts of the diaper being broken away to show interior construction;

FIG. 2 is an enlarged fragmentary perspective view showing a tab fastener of this invention;

FIG. 3 is an enlarged cross-sectional view taken along plane 3—3 in FIG. 2;

FIG. 4 is an enlarged cross-sectional view taken along plane 4—4 in FIG. 1;

FIG. 5 is a fragmentary perspective view illustrating an alternate embodiment of the invention;

FIG. 6 is a perspective view of the diaper of FIG. 1 in a configuration assumed by the diaper when placed about an infant;

FIG. 7 is an enlarged cross-sectional view taken along plane 7—7 in FIG. 5; and

FIG. 8 is an enlarged cross-sectional view taken along plane 8—8 in FIG. 1.

DESCRIPTION OF THE PREFERRED EMBODIMENTS

In the following description, two-digit numerals are used to refer to the embodiment illustrated in FIGS. 1–4, 6 and 8, and three-digit numerals 100–199 are used to refer to the embodiment illustrated in FIGS. 5 and 7. The same last two digits in each numeral designate similar structural elements in the various embodiments.

Disposable diaper 10, illustrated in FIGS. 1 and 6, is of substantially quadrilateral configuration and presents inside surface 12 for direction toward an infant and outside surface 14 for direction away from the infant. Adhesive tabs such as tab 16 are attached to diaper 10 for securing diaper 10 about an infant. Tab 16 is provided with a pressure-sensitive adhesive coating 18 extending over substantially all of one face thereof and presenting a tacky surface facing in the same direction as the diaper inside surface 12.

Referring to FIGS. 1, 3 and 4, diaper 10 comprises a moisture-retaining layer made of moisture-pervious facing sheet 20 which defines the diaper inside surface 12 and overlies absorbent pad 22, and backing sheet 24 which is made of a moisture-impervious material and defines the diaper outside surface 14. Absorbent pad 22 usually is somewhat smaller than backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to backing sheet 24 by means of adhesive beads such as beads 26, glue spots, or in any other convenient manner. For example, if backing sheet 24 is made of a thermoplastic material, facing sheet 20 and pad 22 can be attached thereto by heat bonding.

As illustrated in FIGS. 1-4, adhesive tab 16 comprises backing web 17 coated with pressure-sensitive adhesive layer 18. Fixed end portion 31 of tab 16 is permanently attached by means of adhesive coating or layer 18 to backing sheet 24 on the diaper outside surface 14 at a marginal location thereon, and an unattached opposite end portion of tab 16 comprises free working end 32.

Elongated spacer means 34 are positioned on the adhesive coated surface 18 of free working end 32 and are adhered thereto. As best shown in FIG. 2, spacer means 34 extend between the side edges 28 and 30 of tab 16, form an acute angle $\theta$ with respect to the diaper side margin, and define a plurality of exposed adhesive coated regions 36 on free working end 32 between spacer means 34. Materials such as thread, nylon, or other plastic monofilaments which will releasably adhere to adhesive coated surface 18 and project above the surface thereof are suitable for use as spacer means 34. The spacer means preferably are parallel to each other, uniformly spaced and, if desired, can be positioned on both the fixed end 31 and free working end 32 of tab 16. Alternatively, the spacer means can be a plurality of substantially aligned elongated thread or monofilament segments, or the like, partially embedded in the adhesive layer forming coated surface 18. The spacer means are preferably positioned on the adhesive coated surface 18 of only free working end 32 of the tab. From the standpoint of manufacturing expedience, however, it may be desirable to position spacer means 34 on the entire adhesive coated surface 18 of tab 16.

Free working end 32 includes a distal end portion 40 and adjacent central portion 42 (FIG. 4). As shown in FIGS. 3 and 4, spacer means 34 project outwardly from the adhesive surface 18 of tab 16. When free working end 32 is folded over upon itself to assume the storage position illustrated in FIG. 4, distal end portion 40 is adhesively but releasably secured to central portion 42. Spacer means 34 on distal end portion 40 bridge or cross over similar spacer means on central portion 42 and are in contact therewith at spaced points 44 while other portions of spacer means 34 are in limited adhesive contact, substantially a point or line contact, with juxtaposed regions of adhesive coated surface 18 at a plurality of attachment points 46 between the contact points 44 (FIGS. 1 and 8). Since elongated spacer means 34 project outwardly from the plane of tab 16, it is desirable to provide regions 36 (FIG. 2) the width of which is at least four times the diameter of spacer means 34 so as to facilitate adhesive contact at attachment points 46. Preferably, the width of adhesive regions 36 is about 10 to about 15 times the diameter of spacer means 34.

Distal end portion 40 is readily releasable from central portion 42 to enable free working end 32 of tab 16 to be moved to the working position illustrated in FIGS. 3 and 6 wherein the entire free working end 32 of tab 16 is securable to an opposite end of diaper 10. To facilitate the release of distal end portion 40 from central portion 42, the exposed portions of spacer means 34 can be treated with a release compound, if desired. Usually it is not necessary to do so, however. Also, to prevent accidental lifting of spacer means 34 away from the underlying adhesive surface 18, spacer means 34 can be permanently anchored to the substrate web of free working end 32, if desired.

As illustrated in FIG. 2, spacer means 34 preferably are substantially parallel to each other and are preferably disposed at an angle $\theta$ of about 30° to about 60° with respect to the diaper side margin. More preferably, angle $\theta$ is about 45° so that the spacer means on distal end portion 40 cross the spacer means on opposite end portion 42 at about a right angle when tab 16 is in the storage position to thereby minimize the amount of filament needed on tab 16 for releasable attachment. However, any angle that will give the desired bridging of the spacer means when juxtaposed can be used.

In the embodiment illustrated in FIGS. 5 and 7, disposable diaper 110 has tab 116 comprising backing web 117 provided with adhesive layer 118 and with elongated spacer means 134 including a first set of spacer means 150 on distal end portion 140 and a second set of spacer means 152 on central portion 142 of free working end 132. Spacer means 134 in set 150 are preferably substantially parallel to each other, and spacer means 134 in set 152 are likewise substantially parallel to each other, with set 150 being angularly disposed relative to set 152. The angle between spacer means set 150 and spacer means set 152 is about 90° in the embodiment shown in FIG. 5. One of the pluralities of spacer means 134 such as spacer means 150, is parallel to the side edges 128 and 130 of tab 116.

To facilitate gripping in order to lift distal end portion 40 from opposite end portion 42 to which it is releasably adhered, a gripping means can also be provided on tab 16. As illustrated in FIGS. 1 through 5, distal end portion 40 can be provided with extension 60 which projects beyond outermost edge 62 of adhesive coating 18 and forms a lift tab. Extension 60 provides a gripping means for removing releasable distal end portion 40 from opposite end portion 42 when fastening the diaper about an infant. When tab 16 is in the folded-over storage portion illustrated in FIG. 4, outermost edge 62 of adhesive coating 18 is spaced from margin 64 of facing layer 20 so as to prevent adhesive attachment therebetween, and extension 60 is juxtaposed to diaper inside surface 12 at a marginal location on facing layer 20 to facilitate in gripping the distal end portion 40 of tab 16.

Adhesive tabs suitable for the purposes of the present invention can be made from a wide variety of materials, provided that such materials are sufficiently flexible. Particularly preferred materials for this purpose are polyalkylene webs such as polyethylene sheet, polypropylene sheet, and the like.

The pressure-sensitive adhesive layers such as adhesive coating 18 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Suitable materials for the spacer means can be monofilaments of nylon, polypropylene, polyethylene, fluorinated ethylene-propylene copolymers, and polyesters as well as cotton or fiberglass yarns, segments of thin wires, and the like.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75 to about 98%, the balance being textile length fibers such as rayon as described in U.S. Pat. No. 3,633,348 to Liloia et al.

Facing sheet materials suitable for use in this invention can have fabric weight in the range of about 1 to 5 oz./yd.$^2$ and densities of less than 0.15 g./cc., generally in the range between 0.05 and 0.1 g/cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, non-woven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially co-extensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re.26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomencovering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling distal end portions 40 away from their temporary engagement with central portions 42 of the free working ends 32 of tabs 16. The tabs are then used to secure the diaper in the desired position by simply urging the pressure-sensitive adhesive surfaces in contact with the adjacent outer surface of the diaper. The applied diaper assumes the configuration illustrated in FIG. 6.

The foregoing description and the drawing are illustrative but are not to be taken as limiting. Still other variations and modifications are possible without departing from the spirit and scope of the present invention.

I claim:
1. A disposable diaper which comprises:
    a moisture-impermeable backing sheet forming a diaper outside surface for direction away from an infant when the diaper is worn by that infant;
    a moisture-permeable facing sheet which forms a diaper inside surface for direction toward the infant;
    an absorbent layer positioned between the backing sheet and the facing sheet;
    tab fastener means having side edges, a fixed end secured to said diaper backing sheet, and a free work end, said tab fastener means being provided with a layer of pressure-sensitive adhesive presenting a tacky surface facing in the same direction as the diaper inside surface;
    a plurality of elongated spacer means positioned on said tacky surface in a spaced relationship to one another and adhered thereto, and defining a plurality of exposed adhesive regions between said spacer means;
    said free working end having a distal end portion which is folded over onto an adjacent central por- tion of said free working end and releasably secured thereto in a storage position, and juxtaposed spacer means bridging one another and being in limited contact with a juxtaposed region of said tacky surface at a plurality of attachment points when said free working end is folded over.

2. A disposable diaper as defined in claim 1 wherein said elongated spacer means extend between said side edges of said tab fastener means.

3. A disposable diaper as defined in claim 2 wherein each said spacer means is substantially parallel to the other spacer means.

4. A disposable diaper as defined in claim 2 wherein said spacer means are disposed at an acute angle relative to side margin of the diaper.

5. A disposable diaper as defined in claim 3 wherein said spacer means are uniformly spaced on said tacky surface.

6. A disposable diaper as defined in claim 2 wherein said spacer means are monofilaments.

7. A disposable diaper as defined in claim 3 wherein each said spacer means is disposed at an angle of about 30° to about 60° relative to side margin of the diaper.

8. A disposable diaper as defined in claim 3 wherein each said spacer means forms an angle of about 45° relative to said side margin of the diaper.

9. A disposable diaper as defined in claim 1 wherein said plurality of spacer means includes a first set of substantially parallel spacer means on said distal end of said free working end and a second set of parallel spacer means on said central portion of said free working end, said first set of spacer means being angularly disposed relative to said second set of spacer means.

10. A disposable diaper as defined in claim 9 wherein said angle between said first and second sets of spacer means is about 90°.

11. A disposable diaper as defined in claim 10 wherein one of said sets of spacer means is substantially parallel to said side edges of said tab.

12. A disposable diaper as defined in claim 1 wherein said spacer means are permanently anchored to said tab.

13. A disposable diaper as defined in claim 1 wherein said space between said spacer means has a width at least about four times the diameter of each spacer means.

14. A disposable diaper as defined in claim 1 wherein said tab fastener has a longer longitudinal dimension than said layer of adhesive and provides a lift tab to facilitate gripping said distal end portion for removing said distal end portion from said opposite end portion when fastening said diaper about an infant.

15. A disposable diaper as defined in claim 1 wherein said spacer means are positioned only on said free working end of said tab fastener.

* * * * *